United States Patent
Schenk et al.

[11] Patent Number: 5,875,768
[45] Date of Patent: Mar. 2, 1999

[54] METHOD AND ARRANGEMENT FOR DETERMINING THE SENSITIVITY OF A HYDROCARBON SENSOR FOR AN INTERNAL COMBUSTION ENGINE

[75] Inventors: Rene Schenk, Tamm; Bernd Schumann, Rutesheim, both of Germany

[73] Assignee: Robert Bosch GmbH, Stuttgart, Germany

[21] Appl. No.: 903,934

[22] Filed: Jul. 31, 1997

[30] Foreign Application Priority Data

Aug. 2, 1996 [DE] Germany .......................... 196 31 308.2
Sep. 7, 1996 [DE] Germany .......................... 196 36 416.7

[51] Int. Cl.$^6$ .............................. G01N 7/00; G01N 27/16
[52] U.S. Cl. .......................... 123/688; 73/1.06; 73/23.31; 123/703
[58] Field of Search ..................................... 123/688, 690, 123/703; 73/1.06, 23.31, 23.32; 204/401; 422/98

[56] References Cited

U.S. PATENT DOCUMENTS 4,314,475  2/1982  Karpov et al. .......................... 73/1.06
4,742,808  5/1988  Blumel et al. .......................... 123/688
4,789,939 12/1988  Hamburg .............................. 123/703 X

FOREIGN PATENT DOCUMENTS 3713643 11/1988 Germany .
4342136  6/1995 Germany .
4443941  6/1996 Germany .
2201516  9/1988 United Kingdom .

*Primary Examiner*—Tony M. Argenbright
*Attorney, Agent, or Firm*—Walter Ottesen

[57] ABSTRACT

The invention is directed to a method of determining the sensitivity of a hydrocarbon sensor for an internal combustion engine generating exhaust gas during the operation thereof. The hydrocarbon sensor includes a probe electrode subjected to the exhaust gas and a heater device for heating the probe electrode whereby a voltage (U) is generated in the sensor and is present at the probe electrode with the voltage (U) being a criterion for the concentration of hydrocarbon molecules in the exhaust gas. The voltage (U) present on the probe electrode is short circuited for a short time and the voltage (U) is measured as a function of time to obtain a voltage curve. A conclusion is then drawn as to the sensitivity of the hydrocarbon sensor from the voltage curve. The invention is also directed to an arrangement for carrying out the invention.

9 Claims, 4 Drawing Sheets

METHOD AND ARRANGEMENT FOR DETERMINING THE SENSITIVITY OF A HYDROCARBON SENSOR FOR AN INTERNAL COMBUSTION ENGINE

FIELD OF THE INVENTION

The invention relates first to a method for determining the sensitivity of a hydrocarbon sensor for an internal combustion engine having a heatable probe electrode, which detects hydrocarbon molecules and generates a voltage as a criterion for the concentration of hydrocarbon molecules.

BACKGROUND OF THE INVENTION

United States federal regulations require that the functions of all emission-relevant components (such as injection systems, catalytic converters and the like) of a motor vehicle must be monitored during the operation thereof utilizing on-board means (on-board diagnosis, OBD). For vehicles having internal combustion engines including diesel vehicles, oxidation catalytic converters as well as NOx catalytic converters (so-called denox catalytic converters) are utilized for improving exhaust-gas values. Hydrocarbon sensors (HC sensors) are utilized to monitor the operation of such catalytic converters. These sensors are based essentially on the mixture potential principle and are similar to the lambda probes known per se with respect to their configuration. With an otherwise same configuration, these HC sensors differ from the lambda probe sensors essentially only in the hydrocarbon sensitive electrode coating.

The hydrocarbon concentration in the exhaust gas of an internal combustion engine can be detected by means of these hydrocarbon sensors and from this, a conclusion can be drawn as to the operability, for example, of an oxidation catalytic converter or a denox catalytic converter.

It is problematic with such hydrocarbon sensors that a considerable loss in sensitivity occurs during long-term operation. For a long service life, tolerances develop which are so great that monitoring of the catalytic converters in the context of the OBD is no longer possible. Accordingly, either the deterioration must somehow be prevented or the loss of sensitivity occurring because of deterioration must be compensated in some way in order to make such hydrocarbon sensors more stable for a long period of time.

In a known method for determining the sensitivity of a hydrocarbon sensor, measured values, which are detected by the hydrocarbon sensor and are made erroneous because of its deterioration, are corrected via an elapsed-time counter and a previously determined deterioration characteristic line. For example, for an exchange of the control apparatus and/or of the sensor, it is here however disadvantageous that the elapsed-time counter must always be brought to the correct count which is associated with a considerable complexity.

In another known method, a calibration is carried out for known gas concentrations during operation. This, however, is not possible during driving operation because the emissions of the engine change in the course of time and therefore cannot define a reference.

SUMMARY OF THE INVENTION

It is an object of the invention to improve upon a method for determining the sensitivity of a hydrocarbon sensor for an internal combustion engine in that a reliable statement is achieved in the most technically simple manner as possible as to the sensitivity of the hydrocarbon sensor independently of deterioration and as independently as possible of the detection of additional engine operating data.

The method of the invention is for determining the sensitivity of a hydrocarbon sensor for an internal combustion engine generating exhaust gas during the operation thereof. The hydrocarbon sensor includes a probe electrode subjected to the exhaust gas and a heater device for heating the probe electrode whereby a voltage (U) is generated in the sensor and is present at the probe electrode with the voltage (U) being a criterion for the concentration of hydrocarbon molecules in the exhaust gas. The method includes the steps of: short circuiting the voltage (U) present on the probe electrode for a short time; measuring the voltage (U) as a function of time to obtain a voltage curve; and, drawing a conclusion as to the sensitivity of the hydrocarbon sensor from the voltage curve.

With this measurement method, the dynamic characteristics of the hydrocarbon sensor during operation can be determined in an especially advantageous manner and a conclusion as to the sensitivity of the hydrocarbon sensor can be drawn therefrom. In this way, a compensation of the loss in sensitivity caused by deterioration is possible for hydrocarbon sensors in a manner which is technically simple to realize.

It has been shown that, in the course of time, the sensitivity of the sensor based on disadvantageous changes of the dynamic characteristics of the sensor becomes less. The sensor becomes slower with increased deterioration and therefore less sensitive.

In principle, the time-dependent measurement of the voltage course and the conclusion as to the sensitivity of the sensor from this voltage course can take place in various ways.

The dynamic characteristics of the sensor are detected directly in an especially advantageous embodiment of the method of the invention. In this embodiment, the time is measured which passes until the voltage again reaches a pregiven voltage value after the short circuit and a conclusion as to the sensitivity of the sensor is drawn therefrom. From the time constant measured in this way, a corrective factor can be determined, for example, via a characteristic line and, with this corrective factor, the voltage, which is outputted by the hydrocarbon sensor for subsequent measurements, is multiplied.

A measurement problem can result in that the hydrocarbon concentration during the measurement operation does not always remain constant during an actual driving operation. To deal with this problem, an advantageous embodiment of the method of the invention provides that the measurement is repeatedly carried out and the measurement times, which elapse for each measurement until the voltage at the probe electrode reaches a pregiven measurement value, are determined and averaged and, from the mean value, a conclusion as to the sensitivity of the hydrocarbon sensor is drawn.

Preferably, the pregiven voltage value amounts to approximately ⅔-times the voltage which is present at the probe electrode before applying the short circuit.

The short circuit time advantageously amounts to less than 0.5 seconds.

Another especially advantageous embodiment of the method of the invention considers the changing hydrocarbon concentration during the measurement operation for an actual driving operation. In this embodiment of the method of the invention, operating parameters of the engine, which are detected by an engine control apparatus known per se, are stored at the start of the measurement and compared to operating parameters of the engine detected at the end of the measurement and the time constants, which are obtained for the measurements, are only then considered for further processing when the operating parameters detected at the end differ only by pregiven tolerance values from the operating parameters detected at the start.

Advantageously, the two last-mentioned embodiments of the method can also be combined with each other.

The arrangement of the invention is for determining the sensitivity of a hydrocarbon sensor for an internal combustion engine producing exhaust gas during operation thereof. The hydrocarbon sensor includes a heatable probe electrode for detecting hydrocarbon molecules in the exhaust gas and the probe electrode has an internal resistance ($R_i$) which is a criterion for the concentration of hydrocarbon molecules in the exhaust gas. The arrangement further includes: a switch device connected to the probe electrode which is switchable between a first state wherein the voltage (U) is not short circuited and a second state wherein the voltage (U) is short circuited; control means for generating a drive signal for driving the switch device between the first and second states to short circuit the voltage (U) on the probe electrode for a predetermined time span; and, means for measuring and evaluating the voltage (U) before, during and after the voltage (U) is short circuited.

An especially advantageous embodiment of the invention provides that the control means is part of an engine control apparatus known per se. In this way, additional circuit units are not needed. The switch device is preferably a field effect transistor (FET).

BRIEF DESCRIPTION OF THE DRAWINGS

The invention will now be described with reference to the drawings wherein.

DESCRIPTION OF THE PREFERRED EMBODIMENTS OF THE INVENTION

Figure 4:
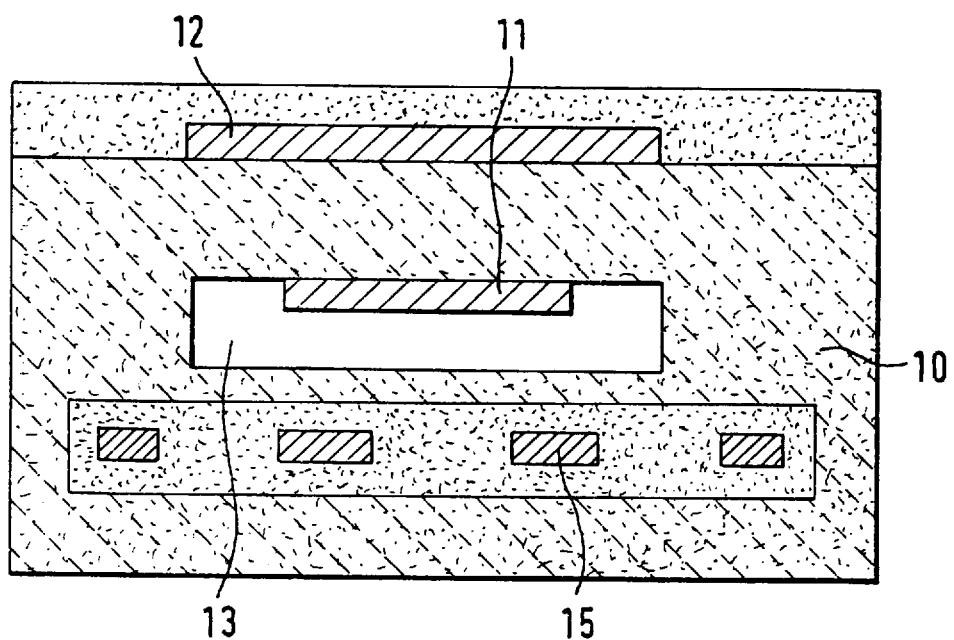

As shown in FIG. 4, a hydrocarbon sensor 2 essentially includes a reference electrode 11, which is fixed on a ceramic body 10, and which is mounted in a reference air channel 13 filled with ambient air. The hydrocarbon sensor further includes a probe electrode 12 which is mounted in the exhaust gas of the engine and a heater device 15 for heating the reference electrode 11 and the probe electrode 12. The heater device 15 is defined by heater resistors made of platinum and embedded in the ceramic so as to be insulated. The ceramic comprises zirconium oxide ($ZrO_2$). This ceramic is an oxygen ion conductor in the heated state. With the heater device 15, the probe is heated to the extent that the oxygen ion conductivity of the ceramic is enabled.

As mentioned above, normal ambient air is present in the reference air channel 13. This ambient air comprises approximately 18% oxygen. A concentration gradient occurs when different oxygen concentrations are present at the reference electrode 11 and at the probe electrode 12. Oxygen particles accept electrons at the side having a high concentration and thereby become oxygen ions. These oxygen ions migrate through the ceramic 10. The oxygen ions again surrender their electrons at the end having the lower oxygen concentration and then leave the ceramic as oxygen molecules and oxidize the hydrocarbon molecules to be measured.

Because of the ion flow, a voltage builds up across the electrodes (11, 12). The electrical field generated thereby between these electrodes exercises a force on the ions which is directed counter to the diffusion. Accordingly, an equilibrium voltage adjusts between the electrodes which can be measured and is a criterion for the hydrocarbon concentration.

It has been shown that the sensitivity of such hydrocarbon sensors reduces with increasing deterioration. Hydrocarbon sensors of this kind are utilized for monitoring catalytic converters in motor vehicles having internal combustion engines in the context of on-board diagnostics (OBD) required in the United States. For this reason, the hydrocarbon sensors must exhibit a measurement sensitivity required for reliable monitoring.

Measurement sensitivity becomes less with increasing deterioration and reliable monitoring is no longer guaranteed because of this reduced sensitivity. For this reason, it is necessary to continuously monitor also the sensitivity of the hydrocarbon sensor. This takes place in an advantageous manner with the arrangement shown in FIG. 1.

Figure 1:
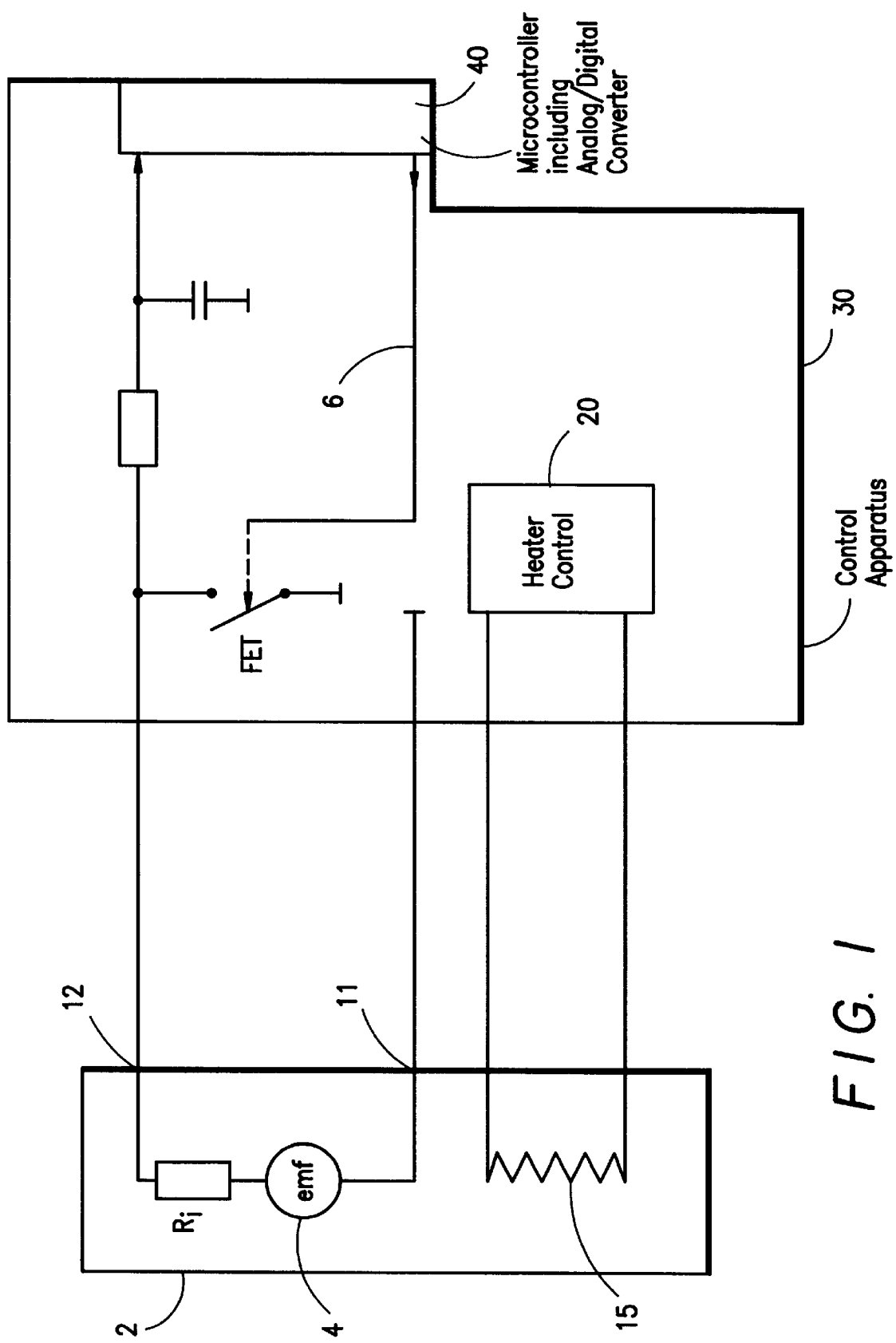
FIG. 1 is a schematic of an embodiment of the arrangement of the invention for determining the sensitivity of a hydrocarbon sensor for an internal combustion engine.

In FIG. 1, reference numeral 2 identifies the hydrocarbon sensor and resistor $R_i$ and voltage source (emf) 4 conjointly define the equivalent circuit for the sensor. The sensor 2 also includes a heater device 15.

The probe electrode 12 outputs a voltage proportional to the hydrocarbon concentration and the alternating-current internal resistance $R_i$ of the probe electrode serves as temperature signal for a heater control 20 in a control apparatus 30. The probe electrode is provided with controlled heating for adjusting a pregiven temperature. As shown in FIG. 1, the probe electrode 12 is connected to the control apparatus 30 which includes a microcontroller 40. The voltage, which is tapped from the probe electrode, is supplied to the microcontroller 40 which includes an analog/digital converter. The microcontroller 40 processes the hydrocarbon signal.

A control line 6 leads from the microcontroller 40 to a field effect transistor FET by means of which the voltage U, which is generated in the sensor 2 and tapped at the probe electrode 12, can be short circuited, as a rule, for <0.5 seconds. Before, during and after this short circuit, the voltage at the probe electrode is continuously supplied to the microcontroller 40.

The evaluation of this voltage can best be explained in connection with FIGS. 2 and 3 which show the voltage trace for a new and old probe, respectively.

Figure 2:
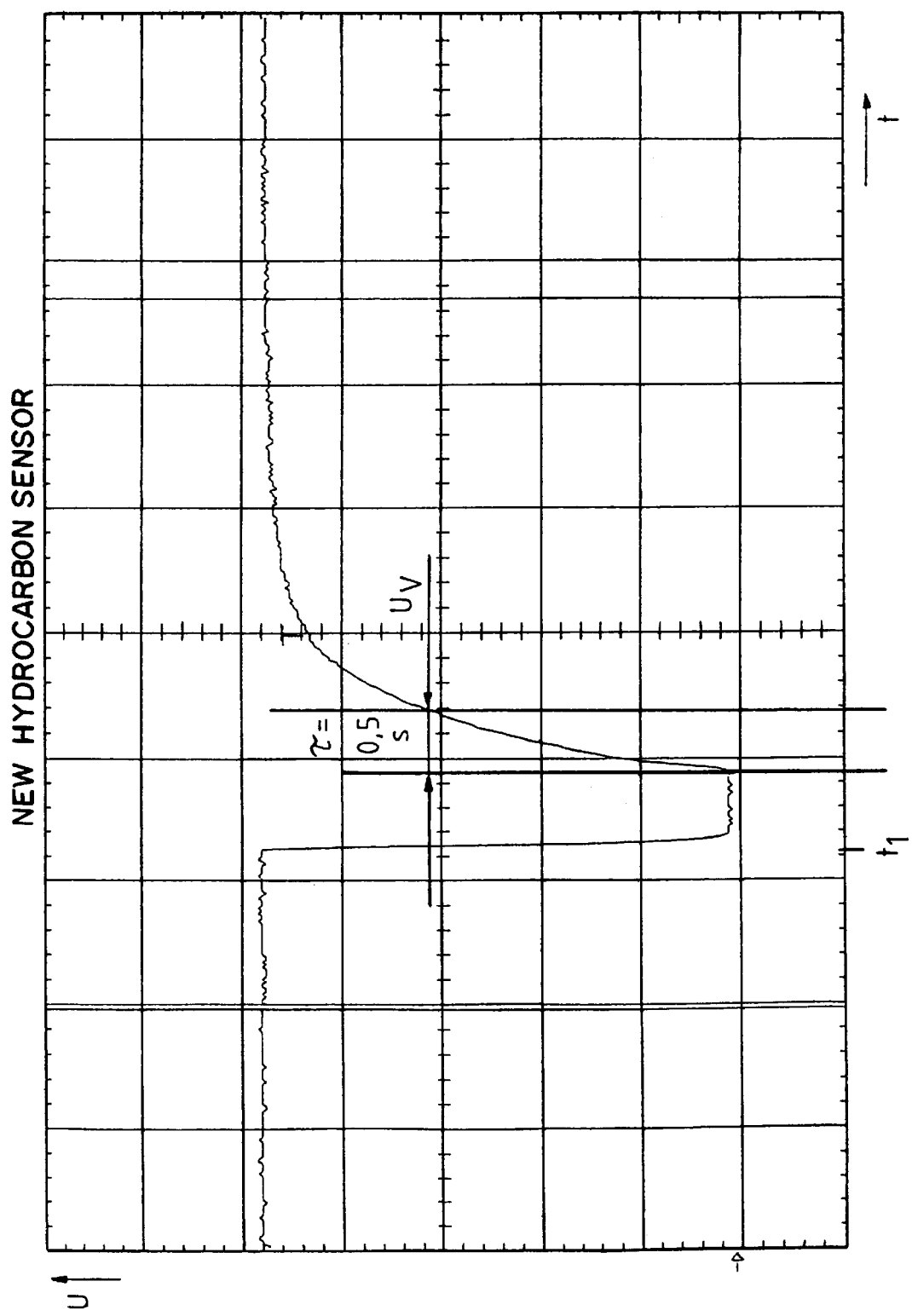
FIG. 2 is a graph showing the voltage trace of a new hydrocarbon sensor obtained with the method of the invention utilizing the arrangement of the invention.

FIG. 2 shows the voltage (probe voltage U), which is generated in the sensor 2 and tapped at the probe electrode 12, as a function of the time (t). As shown in FIG. 2, the probe voltage U drops suddenly because of the short circuit caused by the field effect transistor FET (time $t_1$). After ending the short circuit, the hydrocarbon sensor 2 regenerates itself and therefore so does the voltage U in an essentially exponential manner until it assumes a voltage value which corresponds essentially to the voltage value before the short circuit.

A conclusion is drawn as to the sensitivity of the hydrocarbon sensor based on this voltage trace in that the time ($\tau$)

is measured which has elapsed until the voltage has again reached a pregiven voltage value $U_V$. This voltage value $U_V$ corresponds approximately to ⅔-times the voltage value at the probe electrode before the short circuit. This time ($\tau$) is a criterion for the dynamic of the hydrocarbon sensor which drops with increasing deterioration and therefore is a criterion for the sensitivity of the hydrocarbon sensor.

In the new hydrocarbon sensor shown in FIG. 2, the quantity ($\tau$) has a value of approximately 0.5 seconds.

Figure 3:
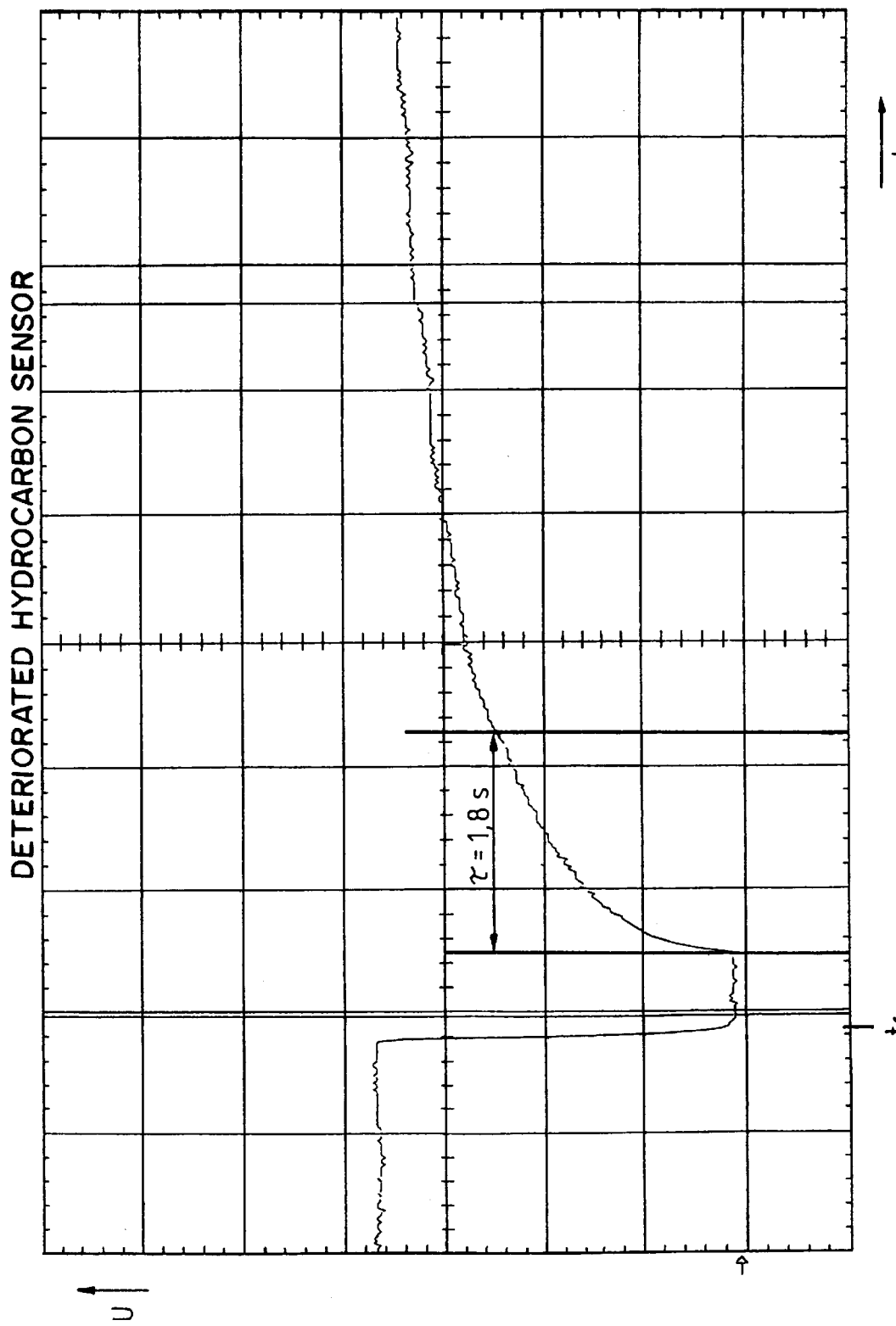
FIG. 3 shows the voltage trace of a deteriorated hydrocarbon sensor obtained with the method of the invention utilizing the voltage trace obtained with the arrangement of the invention; and, FIG. 4 is a schematic showing a hydrocarbon sensor known per se.

In FIG. 3, the voltage trace of a deteriorated hydrocarbon sensor of the same configuration is shown. From FIG. 3, it can be seen that this hydrocarbon sensor regenerates itself significantly slower and, in this way, the probe voltage, after the short circuit, also regenerates significantly slower than the hydrocarbon sensor shown in FIG. 2 because of deterioration for otherwise like measuring conditions. Because of the slowed dynamic of the hydrocarbon sensor shown in FIG. 3, the time constant ($\tau$) is 1.8 seconds and thereby indicates a significantly less sensitive hydrocarbon sensor.

The time constants ($\tau$) determined in this manner can be stored in a characteristic field. A multiplication factor for the voltage taken off at the probe electrode (that is, the hydrocarbon signal) is applied to the output of the characteristic field. In this way, and in a simple manner, a correction of the sensitivity of the hydrocarbon sensor can be provided. The time constant ($\tau$) is first computed and is an input quantity of the characteristic field. A corrective value is taken from the characteristic field and the hydrocarbon value is then corrected therewith.

The measuring sensitivity can be increased and it can be ensured that the hydrocarbon concentration remains constant during the measurement by repeating the measurement several times and forming the mean value of the time constants ($\tau$).

Another embodiment of the measurement provides that, at the start of measurement, the operating parameters of the engine are detected and stored and compared to the operating parameters of the engine at the end of the measurement. If the operating parameters differ by a pregiven value, the measurement is repeated so long until the operating parameters differ only within certain pregiven tolerance values. In this way, it can be ensured that the hydrocarbon concentration remained essentially constant during the measurement.

The two last-mentioned embodiments of the method can also be combined to further increase precision.

The above-mentioned method and arrangement both afford the advantage that the determination of the sensitivity is possible independent of additional devices such as elapsed-time counters and the like and are realized in a relatively simple manner.

It is understood that the foregoing description is that of the preferred embodiments of the invention and that various changes and modifications may be made thereto without departing from the spirit and scope of the invention as defined in the appended claims.

What is claimed is:

1. A method of determining the sensitivity of a hydrocarbon sensor for an internal combustion engine generating exhaust gas during the operation thereof, the hydrocarbon sensor including a probe electrode subjected to the exhaust gas and a heater device for heating said probe electrode whereby a voltage (U) is generated in said sensor and is present at said probe electrode with said voltage (U) being a criterion for the concentration of hydrocarbon molecules in the exhaust gas, the method comprising the steps of:

short circuiting said voltage (U) present on said probe electrode for a short time;

measuring said voltage (U) as a function of time to obtain a voltage curve; and, drawing a conclusion as to the sensitivity of said hydrocarbon sensor from said voltage curve.

2. The method of claim 1, comprising the further steps of:

measuring time elapsed from said short circuiting until said voltage (U) again reaches a pregiven voltage value ($U_V$) corresponding to a time constant ($\tau$); and, drawing a conclusion as to said sensitivity of said sensor from the measured elapsed time.

3. The method of claim 2, comprising the further steps of:

repeating said step of measuring the time elapsed and averaging said time constants ($\tau$) to obtain a mean value thereof; and, drawing a conclusion as to said sensitivity from said mean value.

4. The method of claim 3, wherein said pregiven voltage value ($U_V$) is approximately ⅔ of said voltage (U) present on said probe electrode before said short circuit.

5. The method of claim 4, wherein said short time that said probe electrode is short circuited is less than 0.5 seconds.

6. The method of claim 4, wherein said internal combustion engine includes an engine control apparatus; and, wherein the method comprises the further steps of:

detecting first values of operating parameters of said engine at the start of said measuring step and storing said first values;

detecting said operating parameters of said engine at the end of said measuring step and obtaining a second set of values of said operating parameters and comparing said second set of values to said first set of values; and, utilizing the time constants ($\tau$) obtained from said measurements for further processing when said second values of said operating parameters differ by pregiven tolerance values from said first values of said operating parameters.

7. An arrangement for determining the sensitivity of a hydrocarbon sensor for an internal combustion engine producing exhaust gas during operation thereof, the hydrocarbon sensor including a heatable probe electrode for detecting hydrocarbon molecules in said exhaust gas and said probe electrode having an internal resistance ($R_i$) which is a criterion for the concentration of the hydrocarbon molecules in the exhaust gas, the arrangement comprising:

a switch device connected to said probe electrode and being switchable between a first state wherein said voltage (U) is not short circuited and a second state wherein said voltage (U) is short circuited;

control means for generating a drive signal for driving said switch device between said first and second states to short circuit said voltage (U) on said probe electrode for a predetermined time span; and, means for measuring and evaluating said voltage (U) before, during and after said voltage (U) is short circuited.

8. The arrangement of claim 7, wherein said engine includes a control apparatus and said control means is part of said control apparatus.

9. The arrangement of claim 7, wherein said switch device is a field effect transistor (FET).

* * * * *